US007919116B2

(12) United States Patent
Chen et al.

(10) Patent No.: US 7,919,116 B2
(45) Date of Patent: *Apr. 5, 2011

(54) CONTROLLED RELEASE METFORMIN FORMULATIONS

(75) Inventors: Chih-Ming Chen, Taipei (TW); Xiu Xiu Cheng, Weston, FL (US); Steve Jan, Coral Springs, FL (US); Joseph Chou, Manassas, VA (US)

(73) Assignee: Andrx Labs, LLC, Davie, FL (US)

( * ) Notice: Subject to any disclaimer, the term of this patent is extended or adjusted under 35 U.S.C. 154(b) by 196 days.

This patent is subject to a terminal disclaimer.

(21) Appl. No.: 11/713,143

(22) Filed: Mar. 2, 2007

(65) Prior Publication Data

US 2007/0154548 A1     Jul. 5, 2007

Related U.S. Application Data

(63) Continuation of application No. 09/726,193, filed on Nov. 29, 2000, now abandoned, which is a continuation of application No. 09/594,637, filed on Jun. 15, 2000, now abandoned, which is a continuation of application No. 09/045,330, filed on Mar. 20, 1998, now Pat. No. 6,099,859.

(51) Int. Cl.
*A61K 9/22* (2006.01)
*A61K 31/155* (2006.01)
(52) U.S. Cl. .................................... 424/468; 514/635
(58) Field of Classification Search .......... 424/468; 514/635
See application file for complete search history.

(56) References Cited

U.S. PATENT DOCUMENTS

| 3,174,901 | A |   | 3/1965  | Sterne |
|-----------|---|---|---------|--------|
| 3,621,097 | A |   | 11/1971 | Scott |
| 3,845,770 | A |   | 11/1974 | Theeuwes et al. |
| 3,916,899 | A |   | 11/1975 | Theeuwes et al. |
| 3,950,524 | A |   | 4/1976  | Hitzel et al. |
| 3,952,741 | A |   | 4/1976  | Baker |
| 3,957,853 | A |   | 5/1976  | Bohuon |
| 3,960,949 | A |   | 6/1976  | Ahrens et al. |
| 4,008,719 | A |   | 2/1977  | Theeuwes et al. |
| 4,017,539 | A |   | 4/1977  | Bosies et al. |
| 4,034,758 | A |   | 7/1977  | Theeuwes |
| 4,036,228 | A |   | 7/1977  | Theeuwes |
| 4,058,122 | A |   | 11/1977 | Theeuwes et al. |
| 4,063,064 | A |   | 12/1977 | Saunders et al. |
| 4,077,407 | A |   | 3/1978  | Theeuwes et al. |
| 4,080,472 | A | * | 3/1978  | Bohuon ................. 514/555 |
| 4,088,864 | A |   | 5/1978  | Theeuwes et al. |
| 4,111,201 | A |   | 9/1978  | Theeuwes |

(Continued)

FOREIGN PATENT DOCUMENTS

CA        1103161        6/1981

(Continued)

OTHER PUBLICATIONS

Cantor; Request for Reexamination of U.S. Patent No. 5,955,106; Bloomfield, CT; Oct. 4, 2002.

(Continued)

*Primary Examiner* — Blessing M Fubara
(74) *Attorney, Agent, or Firm* — Florek & Endres PLLC

(57) ABSTRACT

Sustained release pharmaceutical formulations comprising an antihyperglycemic drug or a pharmaceutically acceptable salt thereof are disclosed. The formulations provide therapeutic plasma levels of the antihyperglycemic drug to a human patient over a 24 hour period after administration.

5 Claims, 8 Drawing Sheets

U.S. PATENT DOCUMENTS

| Patent | Kind | Date | Inventor | Ref |
|---|---|---|---|---|
| 4,140,755 | A | 2/1979 | Sheth et al. | |
| 4,160,020 | A | 7/1979 | Ayer et al. | |
| 4,220,648 | A | 9/1980 | Youngdale | |
| 4,248,858 | A | 2/1981 | Guley et al. | |
| 4,327,725 | A | 5/1982 | Cortese et al. | |
| 4,351,825 | A | 9/1982 | Sothmann et al. | |
| 4,357,469 | A | 11/1982 | Schor | |
| 4,369,172 | A | 1/1983 | Schor et al. | |
| 4,389,393 | A | 6/1983 | Schor et al. | |
| 4,404,183 | A | 9/1983 | Kawata et al. | |
| 4,522,625 | A | 6/1985 | Edgren | |
| 4,587,117 | A | 5/1986 | Edgren et al. | |
| 4,608,048 | A | 8/1986 | Cortese et al. | |
| 4,609,374 | A | 9/1986 | Ayer | |
| 4,610,686 | A | 9/1986 | Ayer et al. | |
| 4,612,008 | A | 9/1986 | Wong et al. | |
| 4,615,698 | A | 10/1986 | Guittard et al. | |
| 4,624,847 | A | 11/1986 | Ayer et al. | |
| 4,627,850 | A | 12/1986 | Deters et al. | |
| 4,652,441 | A | 3/1987 | Okada et al. | |
| 4,673,405 | A | 6/1987 | Guittard et al. | |
| 4,692,336 | A | 9/1987 | Eckenhoff et al. | |
| 4,696,815 | A | 9/1987 | Schepky et al. | |
| 4,704,118 | A | 11/1987 | Eckenhoff | |
| 4,708,868 | A | 11/1987 | Brickl et al. | |
| 4,711,782 | A | 12/1987 | Okada et al. | |
| 4,765,989 | A | 8/1988 | Wong et al. | |
| 4,777,049 | A | 10/1988 | Magruder et al. | |
| 4,783,337 | A | 11/1988 | Wong et al. | |
| 4,803,076 | A | 2/1989 | Ranade | |
| 4,828,836 | A | 5/1989 | Elger et al. | |
| 4,834,985 | A | 5/1989 | Elger et al. | |
| 4,839,177 | A | 6/1989 | Colombo et al. | |
| 4,849,227 | A | 7/1989 | Cho | |
| 4,851,229 | A * | 7/1989 | Magruder et al. | 424/457 |
| 4,851,232 | A | 7/1989 | Urquhart et al. | |
| 4,857,336 | A | 8/1989 | Khanna et al. | |
| 4,857,337 | A | 8/1989 | Miller et al. | |
| 4,863,724 | A | 9/1989 | Schepky et al. | |
| 4,865,598 | A | 9/1989 | Eckenhoff | |
| 4,871,549 | A | 10/1989 | Ueda et al. | |
| 4,892,739 | A | 1/1990 | Shah et al. | |
| 4,917,893 | A | 4/1990 | Okada et al. | |
| 4,954,298 | A | 9/1990 | Yamamoto et al. | |
| 4,963,141 | A | 10/1990 | Eckenhoff | |
| 5,007,790 | A | 4/1991 | Shell | |
| 5,024,843 | A | 6/1991 | Kuczynski et al. | |
| 5,028,434 | A | 7/1991 | Barclay et al. | |
| 5,030,452 | A | 7/1991 | Curatolo | |
| 5,055,306 | A * | 10/1991 | Barry et al. | 424/482 |
| 5,071,607 | A | 12/1991 | Ayer et al. | |
| 5,082,668 | A | 1/1992 | Wong et al. | |
| 5,091,190 | A | 2/1992 | Kuczynski et al. | |
| 5,100,669 | A | 3/1992 | Hyon et al. | |
| 5,108,756 | A | 4/1992 | Curatolo | |
| 5,110,597 | A | 5/1992 | Wong et al. | |
| 5,120,548 | A | 6/1992 | McClelland et al. | |
| 5,126,145 | A | 6/1992 | Evenstad et al. | |
| 5,141,752 | A | 8/1992 | Ayer et al. | |
| 5,169,638 | A | 12/1992 | Dennis et al. | |
| 5,178,867 | A | 1/1993 | Guittard et al. | |
| 5,185,158 | A | 2/1993 | Ayer et al. | |
| 5,196,410 | A | 3/1993 | Francoeur et al. | |
| 5,200,194 | A | 4/1993 | Edgren et al. | |
| 5,260,275 | A | 11/1993 | Cooper et al. | |
| 5,304,377 | A | 4/1994 | Yamada et al. | |
| 5,308,348 | A | 5/1994 | Balaban et al. | |
| 5,356,913 | A | 10/1994 | Colca | |
| 5,380,526 | A | 1/1995 | Ise | |
| 5,413,572 | A | 5/1995 | Wong et al. | |
| 5,476,663 | A | 12/1995 | Okada et al. | |
| 5,512,293 | A | 4/1996 | Landrau et al. | |
| 5,543,156 | A | 8/1996 | Roorda et al. | |
| 5,545,413 | A | 8/1996 | Kuczynski et al. | |
| 5,575,987 | A | 11/1996 | Kamei et al. | |
| 5,576,306 | A | 11/1996 | Dressman et al. | |
| 5,582,837 | A | 12/1996 | Shell | |
| 5,591,454 | A | 1/1997 | Kuczynski et al. | |
| 5,594,091 | A | 1/1997 | Igari et al. | |
| 5,611,971 | A | 3/1997 | Maedera et al. | |
| 5,614,578 | A | 3/1997 | Dong et al. | |
| 5,622,657 | A | 4/1997 | Takada et al. | |
| 5,629,319 | A | 5/1997 | Luo et al. | |
| 5,631,020 | A | 5/1997 | Okada et al. | |
| 5,631,021 | A | 5/1997 | Okada et al. | |
| 5,631,224 | A | 5/1997 | Efendic et al. | |
| 5,650,170 | A | 7/1997 | Wright et al. | |
| 5,654,005 | A | 8/1997 | Chen et al. | |
| 5,665,394 | A | 9/1997 | Igari et al. | |
| 5,667,804 | A | 9/1997 | Wong et al. | |
| 5,668,117 | A | 9/1997 | Shapiro | |
| 5,674,900 | A | 10/1997 | Ubillas et al. | |
| 5,681,584 | A | 10/1997 | Savastano et al. | |
| 5,688,518 | A | 11/1997 | Ayer et al. | |
| 5,691,386 | A | 11/1997 | Inman et al. | |
| 5,716,640 | A | 2/1998 | Kamei et al. | |
| 5,716,976 | A | 2/1998 | Bernstein | |
| 5,719,188 | A | 2/1998 | Colca | |
| 5,723,269 | A | 3/1998 | Akagi et al. | |
| 5,747,527 | A | 5/1998 | Inman et al. | |
| 5,783,212 | A | 7/1998 | Fassihi et al. | |
| 5,789,393 | A | 8/1998 | Dressman et al. | |
| 5,814,670 | A | 9/1998 | Colca | |
| 5,837,379 | A | 11/1998 | Chen et al. | |
| 5,840,335 | A | 11/1998 | Wenzel et al. | |
| 5,858,398 | A | 1/1999 | Cho | |
| 5,859,037 | A | 1/1999 | Whitcomb | |
| 5,914,326 | A | 6/1999 | McCarty et al. | |
| 5,916,584 | A | 6/1999 | O'Donoghue et al. | |
| 5,922,769 | A | 7/1999 | Barelli et al. | |
| 5,955,106 | A | 9/1999 | Moeckel et al. | |
| 5,965,584 | A | 10/1999 | Ikeda et al. | |
| 5,972,389 | A | 10/1999 | Shell et al. | |
| 6,010,718 | A | 1/2000 | Al-Razzak et al. | |
| 6,011,049 | A | 1/2000 | Whitcomb | |
| 6,051,597 | A | 4/2000 | Zhang et al. | |
| 6,056,977 | A | 5/2000 | Bhagwat et al. | |
| 6,086,920 | A | 7/2000 | Frisbee et al. | |
| 6,099,859 | A * | 8/2000 | Cheng et al. | 424/464 |
| 6,099,862 | A | 8/2000 | Chen et al. | |
| 6,100,300 | A | 8/2000 | Rogosky | |
| 6,113,941 | A | 9/2000 | Takada et al. | |
| 6,117,451 | A | 9/2000 | Kumar | |
| 6,120,803 | A | 9/2000 | Wong et al. | |
| 6,150,384 | A | 11/2000 | Ikeda et al. | |
| 6,166,042 | A | 12/2000 | Ikeda et al. | |
| 6,166,043 | A | 12/2000 | Ikeda et al. | |
| 6,172,090 | B1 | 1/2001 | Ikeda et al. | |
| 6,191,162 | B1 | 2/2001 | Byrd et al. | |
| 6,197,340 | B1 | 3/2001 | Byrd et al. | |
| 6,239,153 | B1 | 5/2001 | Ikeda et al. | |
| 6,284,275 | B1 | 9/2001 | Chen et al. | |
| 6,287,587 | B2 | 9/2001 | Shigeyuki et al. | |
| 6,340,475 | B2 | 1/2002 | Shell et al. | |
| 6,475,521 | B1 | 11/2002 | Timmins et al. | |
| 6,495,162 | B2 | 12/2002 | Cheng et al. | |
| 6,790,459 | B1 * | 9/2004 | Cheng et al. | 424/468 |
| 6,866,866 | B1 * | 3/2005 | Chen et al. | 424/468 |
| 2001/0024659 | A1 | 9/2001 | Chen et al. | |
| 2002/0051820 | A1 | 5/2002 | Shell et al. | |
| 2004/0052848 | A1 | 3/2004 | Cheng et al. | |
| 2004/0219209 | A1 | 11/2004 | Chen et al. | |
| 2006/0008523 | A1 | 1/2006 | Chen et al. | |
| 2006/0008524 | A1 | 1/2006 | Chen et al. | |
| 2006/0008525 | A1 | 1/2006 | Chen et al. | |
| 2006/0008526 | A1 | 1/2006 | Chen et al. | |
| 2006/0034922 | A1 | 2/2006 | Cheng et al. | |

FOREIGN PATENT DOCUMENTS

| | | |
|---|---|---|
| CA | 2251430 | 2/2000 |
| DE | 2124256 | 11/1972 |
| DE | 4432757 | 3/1996 |
| EP | 0283369 | 9/1988 |
| EP | 0583470 | 2/1994 |
| FR | 2449446 | 9/1980 |
| GB | 1552179 | 9/1979 |
| WO | 9318755 | 9/1993 |

| | | |
|---|---|---|
| WO | 96/08243 | 3/1996 |
| WO | 9632097 | 10/1996 |
| WO | 9718814 | 5/1997 |
| WO | 98/10786 | 3/1998 |
| WO | 98/27982 | 7/1998 |
| WO | 9855107 | 12/1998 |
| WO | 99/03477 | 1/1999 |
| WO | 99/29314 | 6/1999 |
| WO | 9930690 | 6/1999 |
| WO | 99/47125 | 9/1999 |
| WO | 99/47128 | 9/1999 |
| WO | 0012097 | 3/2000 |
| WO | 00/28989 | 5/2000 |

OTHER PUBLICATIONS

Channavajjala; Order Granting/Denying Request for Ex Parte Reexamination in U.S. Patent No. 5,955,106; USPTO; Washington, DC; Dec. 17, 2002.
Cantor; Patent Owner's Statement Preliminary Amendment in Reexamination of U.S. Patent No. 5,955,106; Bloomfield, CT; Feb. 3, 2003.
Channavajjala; Office Action in Reexamination of U.S. Patent No. 5,955,106; USPTO; Washington, DC; Jul. 14, 2003.
Channavajjala; Ex Parte Reexamination Interview Summary in Reexamination of U.S. Patent No. 5,955,106; USPTO; Washington, DC; Aug. 27, 2003.
Reimer; Amendment A in Reexamination of U.S. Patent No. 5,955,106; Bloomfield, CT; Sep. 12, 2003.
Channavajjala; Office Action in Reexamination of U.S. Patent No. 5,955,106; USPTO; Washington, DC; Nov. 25, 2003.
Channavajjala; Ex Parte Reexamination Interview Summary in Reexamination of U.S. Patent No. 5,955,106; USPTO; Washington, DC; Jan. 21, 2004.
Reimer; Interview Summary and Response to Office Action in Reexamination of U.S. Patent No. 5,955,106; Bloomfield, CT; Jan. 26, 2004.
Reimer; Responses to Office Action in Reexamination of U.S. Patent No. 5,955,106; Bloomfield, CT; Jun. 1, 2004 and Jul. 30, 2004.
Channavajjala; Office Action in Reexamination of U.S. Patent No. 5,955,106; USPTO; Washington, DC; Dec. 16, 2004.
Pelletier; Examiner Interview Summary and Response to Office Action in Reexamination of U.S. Patent No. 5,955,106; Bloomfield, CT; Feb. 15, 2005.
Channavajjala; Office Action in Reexamination of U.S. Patent No. 5,955,106; USPTO; Washington, DC; Apr. 7, 2005.
Reimer; Appeal Brief in Reexamination of U.S. Patent No. 5,955,106; Bloomfield, CT; Aug. 8, 2005.
Channavajjala; Examiner's Answer in Reexamination of U.S. Patent No. 5,955,106; USPTO; Washington, DC; Nov. 18, 2005.
Reimer; Reply Brief in Reexamination of U.S. Patent No. 5,955,106; Bloomfield, CT; Jan. 17, 2006.
Channavajjala; Communication from Examiner in Reexamination of U.S. Patent No. 5,955,106; USPTO; Washington, DC; Feb. 21, 2006.
Lane; Decision on Appeal in Reexamination of U.S. Patent No. 5,955,106; USPTO/BPAI; Jan. 9, 2007.
Channavajjala; Notice of Intent to Issue Ex Parte Reexamination Certificate in Reexamination of U.S. Patent No. 5,955,106; USPTO; Washington, DC; Aug. 6, 2007.
USPTO; Ex Parte Reexamination Certificate in U.S. Patent No. 5,955,106; USPTO; Washington, DC; Apr. 8, 2008.
Mejía; Opposition in Costa Rican Equivalent to U.S. Published Patent Appl'n. No. 2005/0226928; Feb. 20, 2008. (with English translation).
Valenzuela; Response to Opposition in Costa Rican Equivalent to U.S. Published Patent Appl'n. No. 2005/0226928; Apr. 24, 2008. (with English translation).
Oyedo and Tapia; Opposition in Chilean Equivalent to U.S. Published Patent Appl'n. No. 2005/0226928; Aug. 17, 2007. (with English translation).
Sureda; Response to Opposition in Chilean Equivalent to U.S. Published Patent Appl'n. No. 2005/0226928; Jan. 30, 2008. (with English translation).

Cuellar; Opposition in Colombian Equivalent to U.S. Patent Nos. 6,790,459 and 6,866,866; Sep. 30, 2004. (English translation only).
Villamizar; Opposition (with supporting documents) in Colombian Equivalent to U.S. Patent Nos. 6,790,459 and 6,866,866; Dec. 28, 2004 and Mar. 29, 2005. (English translation only).
Céspedes De Vergel; Communication from Colombian Patent Office in Opposition in Colombian Equivalent to U. S. Patent Nos. 6,790,459 and 6,866,866; Apr. 22, 2005. (English translation only).
Nachshen; Notice of Opposition to EP Patent No. 0781129 by Strawman Ltd.; Mar. 31, 2004.
Hartz; Notice of Opposition to EP Patent No. 0781129 by Andrx Corp.; Apr. 2, 2004.
Nachshen; Document in support of Strawman Ltd.'s Opposition to EP Patent No. 0781129; Feb. 3, 2005.
EPO; Revocation of EP Patent No. 0781129 based on Oral Proceedings; Apr. 5, 2005.
Hartz; Request for dismissal of appeal by patentee in Opposition to EP Patent No. 0781129 by Andrx Corp.; Jan. 26, 2006.
Nachshen; Requests for dismissal of appeal by patentee in Opposition to EP Patent No. 0781129 by Strawman Ltd.; Feb. 24, 2006 and Apr. 25, 2006.
Hartz; Document in support of Request for dismissal of appeal by patentee in Opposition to EP Patent No. 0781129 by Andrx Corp.; Aug. 9, 2007.
Nachshen; Documents in support of Request for dismissal of appeal by patentee in Opposition to EP Patent No. 0781129 by Strawman Ltd.; Aug. 15, 2007; Aug. 24, 2007; and Sep. 6, 2007.
Losert; Notice of Opposition to EP Patent No. 0781129 by Merck Patent GmbH; Apr. 1, 2004. (foreign language only).
Weiβ; Document in support of patentee in Opposition to EP Patent No. 0781129 by Strawman Ltd., Andrx Corp. and Merck Patent GmbH; Aug. 19, 2004. (foreign language only).
Engl et al.; Document from European Patent Office concerning Opposition to EP Patent No. 0781129 by Strawman Ltd., Andrx Corp. and Merck Patent GmbH; Nov. 19, 2004. (foreign language only).
Weiβ; Documents in support of patentee in Opposition to EP Patent No. 0781129 by Strawman Ltd., Andrx Corp. and Merck Patent GmbH; Feb. 4, 2005 and Mar. 24, 2005. (foreign language only).
EPO; Provision of documents from and minutes of Oral Proceeding in Opposition to EP Patent No. 0781129 by Strawman Ltd., Andrx Corp. and Merck Patent GmbH; Apr. 5, 2005 and May 18, 2005. (foreign language only).
EPO; Decision and grounds for revoking patent in Opposition to EP Patent No. 0781129 by Strawman Ltd., Andrx Corp. and Merck Patent GmbH; Jun. 7, 2005. (foreign language only).
Weiβ; Document in support of patentee in Opposition to EP Patent No. 0781129 by Strawman Ltd., Andrx Corp. and Merck Patent GmbH; Oct. 14, 2005. (foreign language only).
Kahrs; Document in support of Merck Patent GmbH's Opposition to EP Patent No. 0781129; Mar. 3, 2006. (foreign language only).
EPO; Minutes of Oral Proceeding in Opposition to EP Patent No. 0781129 by Strawman Ltd., Andrx Corp. and Merck Patent GmbH; Oct. 8, 2007. (foreign language only).
Weiβ; Documents in support of patentee in Opposition to EP Patent No. 0781129 by Strawman Ltd., Andrx Corp. and Merck Patent GmbH; Aug. 27, 2007 and Sep. 18, 2007. (foreign language only).
Townend; Decision in Opposition to EP Patent No. 0781129 by Strawman Ltd., Andrx Corp. and Merck Patent GmbH; EPO; Jan. 18, 2008. (foreign language only).
Lausenmeyer; Revocation of EP Patent No. 0781129 and termination of the proceedings in Opposition to EP Patent No. 0781129 by Strawman Ltd., Andrx Corp. and Merck Patent GmbH; Feb. 20, 2008. (foreign language only).
Schneider; Oath with exhibits submitted by Merck Patent GmbH in the Opposition to EP Patent No. 0781129; Mar. 17, 2004. (foreign language only).
Anderson et al.; "Cardiovascular actions of chronic intracerebroventricular administration of metformin in normotensive rats"; Pharmacol. Toxicol.; vol. 81(1); pp. 7-12; Jul. 1997.
Balan et al.; "In vitro-in vivo correlation (IVIVC) models for metformin after administration of modified-release (MR) oral dosage forms to healthy human volunteers"; Journal of Pharmaceutical Sciences; vol. 90(8); pp. 1176-1185; 2001.

Dennis et al. "In vitro comparison of extended release pH independent matrix tablets and capsures"; Proc. Int. Symp. Controlled Release Bioact. Mater.; 19th; pp. 301-302; 1992.

Franzetti et al.; "Possible synergistic effect of metformin and enalapril on the development of hyperkaliemic lactic acidosis"; Ddiabetes Res. Clin. Pract.; vol. 38(3); pp. 173-176; Dec. 1997.

Garber et al.; "Efficacy of metformin in type II diabetes: results of a double-blind, placebo-controlled, dose-response trial"; Am. J. Med.; vol. 103(6); pp. 491-497; Dec. 1997.

Gouldson et al.; "Use of cellulose ether containing excipients with microcrystalline cellulose for the production of pellets containing metformin hydrochloride by the process of extrusion-spheronization"; J. Microencapsulation; 1997; vol. 14(2); pp. 137-153.

Hadley et al.; "Treatment of type 2 diabetes: a review of metformin in clinical practice"; J.S.C. Med. Assoc.; vol. 94 (1); pp. 12-15; Jan. 1998.

Hoffman et al.; "Efficacy of 24-week monotherapy with acarbose, metformin, or placebo in dietary-treated NIDDM patients: the Essen-II Study"; Am. J. Med.; vol. 103(6); pp. 483-490; Dec. 1997.

Karttunen et al.; The influence of pharmaceutical formulations on the GI side effects of metformin; Acta Endocrinologica; vol. 94, Suppl. 237; p. 42; Scandinavian University Press; 1980.

Lindner et al.; "Controlled release of drugs from hydrocolloid embeddings"; Pharmazie; vol. 51(5); pp. 263-272; 1996.

Marathe et al.; "Effect of altered gastric emptying and gastrointestinal motility on metformin absorption"; British Journal of Clinical Pharmacology; vol. 50(4); pp. 325-332; Oct. 2000.

Misbin et al.; "Lactic acidosis in patients with diabetes treated with metformin"; N. Engl. J. Med.; vol. 338(4); pp. 265-266; Jan. 22, 1998.

Moeckel et al.; "Zero-order drug release from hydrocolloid matrices"; Pharm. Res.; vol. 10(7); pp. 1066-1070; 1993.

Noel, D.S.; "Kinetic study of normal and sustained release dosage forms of metformin in normal subjects"; Journal of International Biomedical Informational Data; pp. 9-20; 1980.

Li et al.; "Influence of drug properties and routes of drug administration on the design of sustained and controlled release systems"; Part I, Chapter 1, Subchapters V-VI; pp. 12-36; Controlled Drug Delivery Fundamentals and Applications, 2nd ed.; Robinson and Lee (editors); Marcel Dekker, Inc.; 1987.

Sambol et al.; "Food intake and dosage level, but not tablet vs solution dosage form, affect the absorption of metformin HCl in man"; British Journal of Clinical Pharmacology; vol. 42(4); pp. 510-512; Oct. 1996.

Shen et al.; "Clinical Pharmacology of Oral Antidiabetic Agents (First of Two Parts)"; The New England Journal of Medicine; vol. 296(9); pp. 493-497; Mar. 3, 1977.

Sirtori et al.; "Disposition of metformin (N,N-dimethylbiguanide) in man"; Clin Pharmacol Ther.; vol. 24; pp. 683-693; 1978.

Timmins et al.; "Optimization and characterization of a pH-independent extended-release hydrophilic matrix table"; Pharm. Dev. & Tech.; vol. 2(1); pp. 25-31; 1997.

Vidon et al.; "Metformin in the digestive tract"; Diabetes Research and Clinical Practice; vol. 4(3); pp. 223-229; Feb. 19, 1988.

Vigneri et al.; "Treatment of NIDDM patients with secondary failure to glyburide: comparison of the addition of either metformin or bed-time NPH insulin to glyburide"; Diabete Metabol.; vol. 17(1); pp. 232-234; May 1991.

Baraldi et al.; "Studio Dell'Effetto Antiaterosclerotico Della Metformina Nel Diabete Mellito Dell'Adulto In Fase Iniziale"; Clin. Ter.; vol. 92(6); pp. 657-669; Mar. 31, 1980.

Cavaliere et al.; "Dati preliminari rilevati su due gruppi di diabetici riguardanti l'aggregazione piastrinica in rapport con la retinopatia ed eventale rapport con la terapia antidiabetica"; Minerva. Med.; vol. 69(28); pp. 1923-1928; Jun. 2, 1978.

Diem; "Medikamentöse Therapie des Typ-II-Diabetes: Tabletten, Insulin oder Kombination"; Schweizerische Rundshau Fur Medizin Praxis; vol. 83(2); pp. 68-71; Jan. 1994.

Fearnley; "Aspetti fisiologici e farmacologici della fibrinolisi"; Clin. Ter.; vol. 57(3); pp. 205-225; May 15, 1971.

De Pinho et al.; "Development and biopharmaceutical evaluation of controlled release tablets of metformin hydrochloride using a dissolution medium with gradual pH variation"; Rev. Bras. Clenc. Farm.; vol. 35(1); pp. 101-109; 1999.

Boraie et al.; "Study of the release mechanism of a water soluble drug from hydroxypropylmethylcellulose matrices"; Alex. J. Pharm. Sci.; vol. 6(2); pp. 213-219; Jun. 1992.

Pentikäinen et al.; "Pharmacokinetics of Metformin After Intravenous and Oral Administration to Man"; Eur. J. Clin. Pharmacol; vol. 16; pp. 195-202; 1979.

Complaint filed in C.A. No. 1:09-cv-00037-JJF in the United States District Court for the District of Delaware on Jan. 15, 2009 in case styled "*Sciele Pharma, Inc. et al.* v. *Lupin Ltd. et al.*" for alleged infringement of U.S. Patent Nos. 6,099,859 and 6,866,866.

Bailey et al.; "Metformin"; The New England Journal of Medicine; vol. 334; pp. 574-579; Feb. 29, 1996.

Briscoe et al.; "A retrospective analysis of the efficacy and safety of metformin in the African-American patient"; J. Natl. Med. Assoc.; vol. 89(11); pp. 728-730; Nov. 1997.

Campbell et al.; "Metformin: A New Oral Biguanide"; Clinical Therapeutics; vol. 18; No. 3; pp. 360-371; May 1996.

Chiao; "Sustained-release drug delivery systems"; Remington: the science and practice of pharmacy; Mack Publishing Co.; Easton, PA; pp. 1660-1669; 1995.

Dunn et al.; Metformin: A review of its pharmacological properties and therapeutic use in non-insulin-dependent diabetes mellitus; Drugs; ADIS International, Ltd.; vol. 49(5); pp. 721-749; May 1995.

Karttunen et al.; "The pharmacokinetics of metformin: a comparision of the properties of a rapid-release and a sustained-release preparation"; International Journal of Clinical Pharmacology, Therapy & Toxicology; vol. 21(1); pp. 31-36; Jan. 1983.

McCarty Exploring complementary therapeutic strategies for the treatment of type II diabetes and prevention of its complications; Medical Hypotheses; vol. 49; pp. 143-153; 1997.

Kastrup; "Antidiabetic Agents"; Drug Facts and Comparisons; St. Louis, MO; pp. 635-642; 1999.

Scheen; "Clinical pharmacokinetics of metformin"; Clinical Pharmacokinetics; vol. 30(5); pp. 359-371; May 1996.

CDER/FDA; Approval letter on labeling revision to Bristol-Myers Squibb on NDA 21-202; Supplement 001; Apr. 19, 2001.

CDER/FDA; Approval letter on labeling revision to Bristol-Myers Squibb on NDA 21-202; Supplement 011 and 013; Mar. 19, 2004.

CDER/FDA; Approval letter to Bristol-Myers Squibb Co. on NDA 21-202; Supplement 000; Oct. 13, 2000.

CDER/FDA; Approved Label for Glucophage/Glucophage XR; NDA 21-202; Supplement 000; Oct. 13, 2000.

CDER/FDA; Approval letter on formulation revision to Bristol-Myers Squibb on NDA 21-202; Supplement 008; Apr. 11, 2003.

CDER/FDA; Approval letter on labeling revision to Bristol-Myers on NDA 21-202; Supplement 003; Jan. 8, 2002.

Approved Label for Glucophage/Glucophage XR; NDA 21-202; Supplement 008; labeling revision; Apr. 11, 2003.

Approved Label for Glucophage/Glucophage XR; NDA 21-202; Supplement 011 & 013; Mar. 19, 2004.

Pentikainen; "Bioavailability of metformin. Comparison of solution, rapidly dissolving tablet, and three sustained release products"; International Journal of Clinical Pharmacology, Therapy and Toxicology; vol. 24 (4); pp. 213-220; 1986.

Bristol-Myers Squibb; The Diabetes Monitor; 1995.

Threkeld (editor); "Hormones, Antidiabetic Agents, Biguanides, Metformin HCl"; Facts and Comparisons Drug Information; May 1995; pp. 130n-130u.

Physicians' Desk Reference; "Glucophage"; 50th ed.; pp. 752-757; 1996.

Physicians' Desk Reference; 52nd Ed.; pp. 794-800; 1217-1219; 2182-2186; 1998.

Physicians' Desk Reference, 54th Ed.; pp. 831-835; 2000.

Physicians' Desk Reference; "Glucophage XR"; 56th Ed.; pp. 1080-1086; 2002.

STN registry search for metformin; 2003.

Andrx Pilot Biostudy Data (20 pages); 1997.

Thurman K. Page; International Search Report in PCT/US99/06024; USPTO; Washington, DC; 1 pg.; Jun. 24, 1999.

Thurman K. Page; International Preliminary Examination Report in PCT/US99/06024; USPTO; Washington, DC; 3 pgs.; Feb. 2, 2000.

P. Stienon; Supplementary European Search Report in EP99912705; EPO; The Hague; 2 pgs.; Mar. 24, 2006.

Boden et al.; "Evidence for a Circadian Rhythm of Insulin Insensitivity in Patients with NIDDM Caused by Cyclical Changes in Hepatic Glucose Production"; Diabetes; Aug. 1996; pp. 1044-1050; vol. 45.

Rohm GmbH & Co. KG; "Specifications and Test Methods for EUDRAGIT® RL 100 and EIDRAGIT® RL PO, EUDRAGIT® RS 100 and EUDRAGIT® RS PO"; http://www.roehm.com; Sep. 2004; pp. 1-4; Rohm GmbH & Co. KG; Darmstadt, Germany.

Firth et al.; "Postprandial Hyperglycemia in Patients with Noninsulin-dependent Diabetes Mellitus: Role of Hepatic and Extrahepatic Tissues"; J. Clin. Invest.; May 1986; pp. 1525-1532; vol. 77; The American Society for Clinical Investigation, Inc.

D. Christopher Daly, Lupin Ltd.'s Notice of Paragraph IV Certification for U.S. Patent Nos. 6,099,859; 6,495,162; 6,790,459; and 6,866,866; 31 pages; Dec. 3, 2008; Schiff Hardin LLP, Washington, DC.

Steven H. Flynn, Mylan Pharmaceuticals, Inc.'s Notice of Paragraph IV Certification for U.S. Patent Nos. 6,099,859; 6,495,162; 6,790,459; and 6,866,866; 138 pages; Jan. 4, 2010; Mylan Pharmaceuticals, Inc.; Morgantown, WV.

Reaven et al.; "Measurement of Plasma Glucose, Free Fatty Acid, Lactate, and Insulin for 24 h in Patients With NIDDM"; Diabetes; Aug. 1988; pp. 1020-1024; vol. 37.

J.S. Saini; "Management guidelines for use of oral hypoglycemic agents (OHA) in complex clinical situations and important drug interactions with OHA's"; Intnl. J. Diab. Dev. Countries; 1991; pp. 23-24; vol. 11.

Stumvoll et al.; "Metabolic Effects of Metformin in Non-Insulin-Dependent Diabetes Mellitus"; New England Journal of Medicine; Aug. 31, 1995; pp. 550-554; vol. 333(9).

KH Yuen et al.; "Relating In Vitro/In Vivo Data of Two Controlled-Release Metformin Formulations"; Drug Development and Industrial Pharmacy; 1999; pp. 613-618; vol. 25(5); Marcel Dekker, Inc.

Abdallah et al.; "Preparation and evaluation of metformin hydrochloride controlled-release tablets"; S.T.P. Pharma.; vol. 4(1); pp. 15-20; 1988.

Bristol-Myers Squibb Co.; Glucophage® (Metforming hydrochloride tablets); Glucophage® XR (Metformin hydrochloride extended-release tablets); Jul. 2002.

Bristol-Myers Squibb Co.; Glucophage® (Metforming hydrochloride tablets); Glucophage® XR (Metformin hydrochloride extended-release tablets); Apr. 2003.

Bristol-Myers Squibb Co.; Glucophage® (Metforming hydrochloride tablets); Glucophage® XR (Metformin hydrochloride extended-release tablets); Oct. 2000.

Bristol-Myers Squibb Co.; Glucophage® (Metforming hydrochloride tablets); Glucophage® XR (Metformin hydrochloride extended-release tablets); Jun. 2001.

Carstensen; Introduction to Pharmaceutical Principles of Solid Dosage Forms; pp. xv-xviii; Technomic Publishing Co., Inc.; Lancaster, PA; 1993.

CDER; Approval Package for Application No. 020357/S006; Glucophage Tablets (Metformin Hydrochloride) by Bristol-Myers Squibb Co.; Approved Nov. 6, 1997.

Dow; Formulating for controlled release with Methocel cellulose ethers; 1987.

Dow; Formulating for controlled release with Methocel premium cellulose ethers; 1995.

Eastman; Eastman Cellulose Acetate for Coatings; "Types and Typical Properties"; Pub. No. E-305; Jan. 1996.

Eastman; Eastman Cellulose Esters: The Performance Edge; Pub. No. E-325A; Jul. 2003.

Eastman; Eastman Cellulose Esters: The Performance Edge; Pub. No. PCI-105A; Oct. 2003.

Electronic Medicines Compendium; Merck Pharmaceuticals: Glucophage; 10 pgs.; Jun. 25, 2003.

Inzucchi et al.; "Efficacy of metabolic effects of metformin and troglitazone in type II diabetes mellitus"; New England Journal of Medicine; vol. 338; 1998.

Jantzen et al.; "Osmotically Controlled Systems"; Modern Pharmaceutics, 3rd Ed., Revised and Expanded; ed. Banker and Rhodes; pp. 575-609; vol. 72; Marcel Dekker, Inc.; New York, NY; 1996.

Kibbe; Handbook of Pharmaceutical Excipients; pp. 386-388; 3rd. Ed.; 1999.

Koski; "Practical review of oral antihyperglycemic agents for type 2 diabetes mellitus"; Review of oral antihyperglycemic agents; Diabetes Educator; vol. 32(6): pp. 869-876; Nov./Dec. 2006.

Lucis; "The Status of Metformin in Canada"; Can. Med. Assoc. J.; vol. 128, pp. 24-26; Jan. 1, 1983.

Metformin from the International Drug Directory; 1992/93.

Otaya et al.; "A dynamic study of the compressed tablet (Part II): The relationship between granule moisture and capping"; Ann. Repts. Shionogi Research Lab.; vol. 1; pp. 462-464; 1954.

Renewal of product license No. 3759/0012-13; Mar. 2, 1988.

Shin-Etsu Chemical Co., Ltd.; Metolose SR: Sustained release agent for matrix system; 1993.

Timmins et al.; "Evaluation of the granulation of a hydrophilic matrix sustained-release tablet"; Drug Dev. & Ind. Pharm.; vol. 17(4); pp. 531-550; 1991.

Tucker et al.; "Metformin kinetics in healthy subjects and in patients with diabetes mellitus"; Br J Clin Pharmacol; vol. 12; pp. 235-246; 1981.

United Kingdom Prospective Diabetes Study Group; "United Kingdom Prospective Diabetes Study 24: a 6-year, randomized, controlled trial comparing sulfonylurea, insulin, and metformin therapy in patients with newly diagnosed type 2 diabetes that could not be controlled with diet therapy"; Ann. Intern. Med.; vol. 128(3); pp. 165-175; Feb. 1, 1998.

Vilkov; Declaration of Zalman Vilkov; 2 pgs.; Sep. 19, 2005.

Vilkov; Second Declaration of Zalman Vilkov Pursuant to 37 CFR 1.32; 5 pgs.; Jul. 29, 2004.

Venkat et al.; Lasers Accelerate Extended-Release Tablet Development; Pharmaceutical Processing; Sep. 2000.

Yuan et al.; "Sustained-release tablets via direct compression: a feasibility study using cellulose acetate and cellulose acetate butyrate"; Pharmaceutical Technology; Oct. 2000.

Pharmaceutical Processing: New Technology for the Pharmaceutical Industry; Jun. 2000.

Lipha; "Glucophage Retard"; Partie II; Documentation Chimique, Pharmaceutique et Biologique; Jan. 11, 1990.

Repertorio Farmaceutico Italiano, Refi 7th Edizione; Farmindustria Associazione Nazionale dell'Industria Farmaceutica; Entries: Glucophage, Metforal; 1993.

"Bundesverand der Pharmazeutischen Industrie e.V."; publ.-Rote Liste 1993; Aulendorf/Wurtt; 1993.

"Bundesverand der Pharmazeutischen Industrie e.V."; publ.-Rote Liste 1994; Aulendorf/Wurtt; 1994.

Vidal, 67th Ed.; Editions du Vidal; Entries: Glucidoral, Glucinan, Glucophage, Glucophage Retard, Stagid; pp. 606-609 and 1281-1282; 1991.

* cited by examiner

CONTROLLED RELEASE METFORMIN FORMULATIONS

The present application is a continuation of U.S. Ser. No. 09/726,193, filed Nov. 29, 2000 now abandoned, which is a continuation of U.S. Ser. No. 09/594,637 filed Jun. 15, 2000 now abandoned, which is a continuation of U.S. Ser. No. 09/045,330 filed Mar. 20, 1998, now issued as U.S. Pat. No. 6,099,859, the disclosures of which are hereby incorporated by reference.

BACKGROUND OF THE INVENTION

The present invention relates to controlled release unit dose formulations containing an antihyperglycemic drug. More specifically, the present invention relates to an oral dosage form comprising a biguanide such as metformin or buformin or a pharmaceutically acceptable salt thereof such as metformin hydrochloride or the metformin salts described in U.S. Pat. Nos. 3,957,853 and 4,080,472 which are incorporated herein by reference.

In the prior art, many techniques have been used to provide controlled and extended-release pharmaceutical dosage forms in order to maintain therapeutic serum levels of medicaments and to minimize the effects of missed doses of drugs caused by a lack of patient-compliance.

In the prior art are extended release tablets which have an osmotically active drug core surrounded by a semipermeable membrane. These tablets function by allowing a fluid such as gastric or intestinal fluid to permeate the coating membrane and dissolve the active ingredient so it can be released through a passageway in the coating membrane or if the active ingredient is insoluble in the permeating fluid, pushed through the passageway by an expanding agent such as a hydrogel. Some representative examples of these osmotic tablet systems can be found in U.S. Pat. Nos. 3,845,770, 3,916,899, 4,034,758, 4,077,407 and 4,783,337. U.S. Pat. No. 3,952,741 teaches an osmotic device wherein the active agent is released from a core surrounded by a semipermeable membrane only after sufficient pressure has developed within the membrane to burst or rupture the membrane at a weak portion of the membrane.

The basic osmotic device described in the above cited patents have been refined over time in an effort to provide greater control of the release of the active ingredient. For example U.S. Pat. Nos. 4,777,049 and 4,851,229, describe an osmotic dosage form comprising a semipermeable wall surrounding a core. The core contains an active ingredient and a modulating agent wherein the modulating agent causes the active ingredient to be released through a passageway in the semipermeable membrane in a pulsed manner. Further refinements have included modifications to the semipermeable membrane surrounding the active core such as varying the proportions of the components that form the membrane, i.e U.S. Pat. Nos. 5,178,867, 4,587,117 and 4,522,625 or increasing the number of coatings surrounding the active core, i.e 5,650,170 and 4,892,739.

Although vast amounts of research has been performed on controlled or sustained release compositions and in particular on osmotic dosage forms, very little research has been performed in the area of controlled or sustained release compositions that employ antihyperglycemic drugs.

The limited work on controlled or sustained release formulations that employ antihyperglycemic drugs such as metformin hydrochloride has been limited to the combination of the antihyperglycemic drug and an expanding or gelling agent to control the release of the drug from the dosage form. This limited research is exemplified by the teachings of WO 96/08243 and by the GLUCOPHAGE® product which is a commercially available product from Bristol-Myers Squibb Co. containing metformin HCl.

It is reported in the 50th Edition of the Physicians' Desk Reference, copyright 1996, p. 753, that food decreases the extent and slightly delays the absorption of metformin delivered by the GLUCOPHAGE® dosage form. This decrease is shown by approximately a 40% lower peak concentration and a 25% lower AUC in plasma and a 35 minute prolongation of time to peak plasma concentration following administration of a single GLUCOPHAGE® tablet containing 850 mg of metformin HCl with food compared to the similar tablet administered under fasting conditions.

It is an object of the present invention to provide a controlled or sustained release formulation for an antihyperglycemic drug wherein the bioavailability of the drug is not decreased by the presence of food.

It is a further object of the present invention to provide a controlled or sustained release formulation for an antihyperglycemic drug that does not employ an expanding polymer.

It is also a further object of the present invention to provide a controlled or sustained release formulation for an antihyperglycemic drug that can provide continuous and non-pulsating therapeutic levels of an antihyperglycemic drug to an animal or human in need of such treatment over a twelve hour to twenty-four hour period.

It is an additional object of the present invention to provide a controlled or sustained release formulation for an antihyperglycemic drug that obtains peak plasma levels approximately 8-12 hours after administration.

It is also an object of this invention to provide a controlled or sustained release pharmaceutical tablet having only a homogeneous osmotic core wherein the osmotic core component may be made using ordinary tablet compression techniques.

SUMMARY OF THE INVENTION

The foregoing objectives are met by a controlled release dosage form comprising:
  (a) a core comprising:
    (i) an antihyperglycemic drug;
    (ii) optionally a binding agent; and
    (iii) optionally an absorption enhancer;
  (b) a semipermeable membrane coating surrounding the core; and
  (c) at least one passageway in the semipermeable membrane.

The dosage form of the present invention can provide therapeutic levels of the antihyperglycemic drug for twelve to twenty-four hour periods and does not exhibit a decrease in bioavailability if taken with food. In fact, a slight increase in the bioavailability of the antihypoglycemic drug is observed when the controlled release dosage form of the present invention is administered with food. In a preferred embodiment, the dosage form will be administered once a day, ideally with or after a meal and most preferably with or after the evening meal, and provide therapeutic levels of the drug throughout the day with peak plasmas levels being obtained between 8-12 hours after administration.

DETAILED DESCRIPTION OF THE INVENTION

Figure 1:
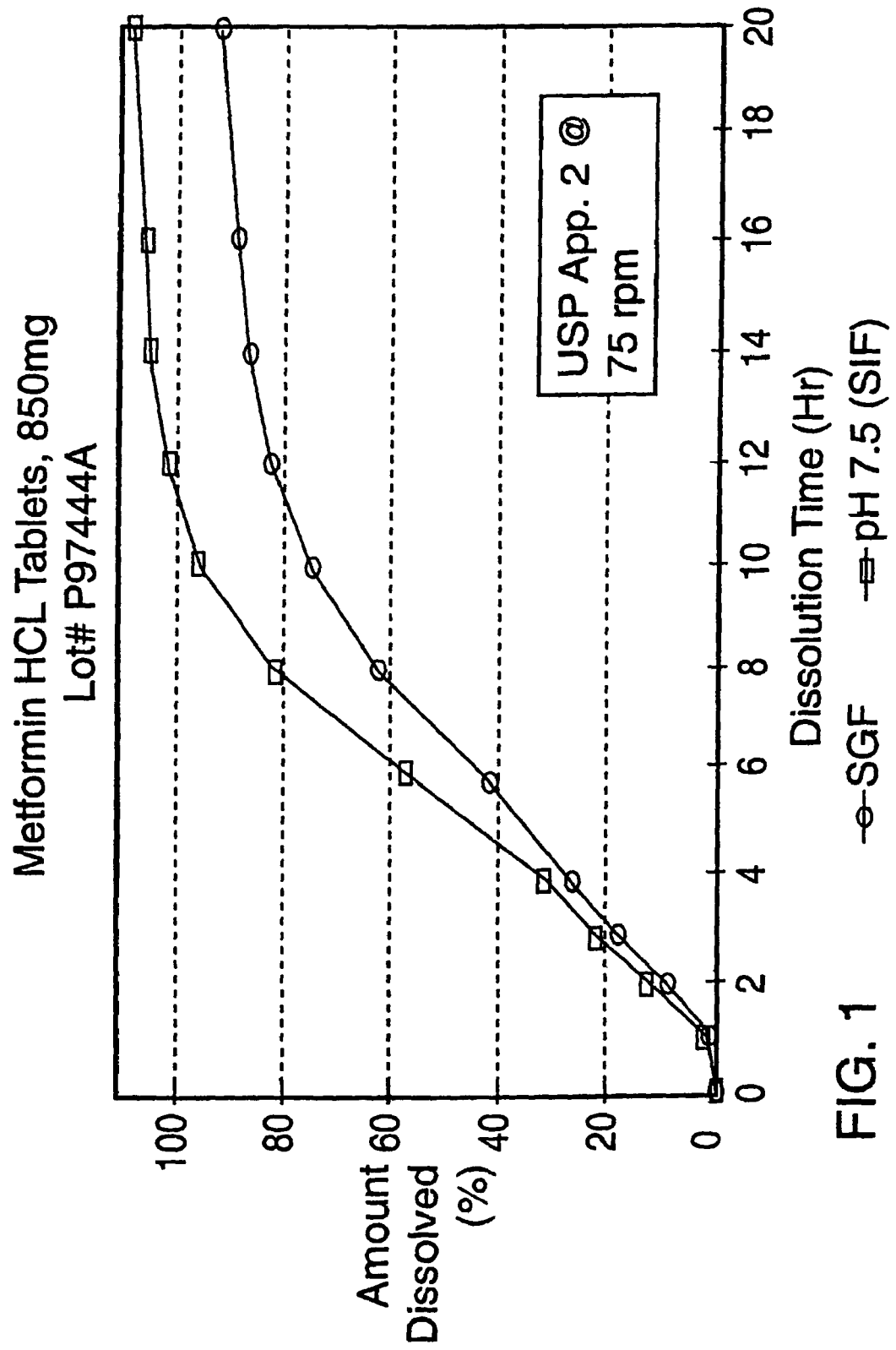
FIG. 1 is a graph which depicts the dissolution profile in simulated intestinal fluid (pH 7.5 phosphate buffer) and simulated gastric fluid (SGF) of the formulation described in Example 1 as tested according to the procedure described in United States Pharmacopeia XXIII, Apparatus 2 @ 75 rpm.

The term antihyperglycemic drugs as used in this specification refers to drugs that are useful in controlling or managing noninsulin-dependent diabetes mellitus (NIDDM). Preferably, the antihyperglycemic drug is a biguanide such as metformin or buformin or a pharmaceutically acceptable salt thereof such as metformin hydrochloride.

The binding agent may be any conventionally known pharmaceutically acceptable binder such as polyvinyl pyrrolidone, hydroxypropyl cellulose, hydroxyethyl cellulose, ethylcellulose, polymethacrylate, waxes and the like. Mixtures of the aforementioned binding agents may also be used. The preferred binding agents are water soluble such as polyvinyl pyrrolidone having a weight average molecular weight of 25,000 to 3,000,000. The binding agent comprises approximately about 0 to about 40% of the total weight of the core and preferably about 3% to about 15% of the total weight of the core.

The core may optionally comprise an absorption enhancer. The absorption enhancer can be any type of absorption enhancer commonly known in the art such as a fatty acid, a surfactant, a chelating agent, a bile salt or mixtures thereof. Examples of some preferred absorption enhancers are fatty acids such as capric acid, oleic acid and their monoglycerides, surfactants such as sodium lauryl sulfate, sodium taurocholate and polysorbate 80, chelating agents such as citric acid, phytic acid, ethylenediamine tetraacetic acid (EDTA) and ethylene glycol-bis (β-aminoethyl ether)-N,N,N,N-tetraacetic acid (EGTA). The core comprises approximately 0 to about 20% of the absorption enhancer based on the total weight of the core and most preferably about 2% to about 10% of the total weight of the core.

The core of the present invention which comprises the antihyperglycemic drug, the binder which preferably is a pharmaceutically acceptable water soluble polymer and the absorption enhancer is preferably formed by wet granulating the core ingredients and compressing the granules with the addition of a lubricant into a tablet on a rotary press. The core may also be formed by dry granulating the core ingredients and compressing the granules with the addition of a lubricant into tablets or by direct compression.

Other commonly known excipients may also be included into the core such as lubricants, pigments or dyes.

The homogeneous core is coated with a semipermeable membrane; preferably a modified polymeric membrane to form the controlled release tablet of the invention. The semipermeable membrane is permeable to the passage of an external fluid such as water and biological fluids and is impermeable to the passage of the antihyperglycemic drug in the core. Materials that are useful in forming the semipermeable membrane are cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, and cellulose acetate butyrate. Other suitable polymers are described in U.S. Pat. Nos. 3,845,770, 3,916,899, 4,008,719, 4,036,228 and 4,11210 which are incorporated herein by reference. The most preferred semipermeable membrane material is cellulose acetate comprising an acetyl content of 39.3 to 40.3%, commercially available from Eastman Fine Chemicals.

In an alternative embodiment, the semipermeable membrane can be formed from the above-described polymers and a flux enhancing agent. The flux enhancing agent increases the volume of fluid imbibed into the core to enable the dosage form to dispense substantially all of the antihyperglycemic drug through the passageway and/or the porous membrane. The flux enhancing agent can be a water soluble material or an enteric material. Some examples of the preferred materials that are useful as flux enhancers are sodium chloride, potassium chloride, sucrose, sorbitol, mannitol, polyethylene glycol (PEG), propylene glycol, hydroxypropyl cellulose, hydroxypropyl methycellulose, hydroxypropyl methycellulose phthalate, cellulose acetate phthalate, polyvinyl alcohols, methacrylic acid copolymers and mixtures thereof. The preferred flux enhancer is PEG 400.

The flux enhancer may also be a drug that is water soluble such as metformin or its pharmaceutically acceptable salts or a drug that is soluble under intestinal conditions. If the flux enhancer is a drug, the present dosage form has the added advantage of providing an immediate release of the drug which is selected as the flux enhancer.

The flux enhancing agent comprises approximately 0 to about 40% of the total weight of the coating, most preferably about 2% to about 20% of the total weight of the coating. The flux enhancing agent dissolves or leaches from the semipermeable membrane to form paths in the semipermeable membrane for the fluid to enter the core and dissolve the active ingredient.

The semipermeable membrane may also be formed with commonly known excipients such a plasticizer. Some commonly known plasticizers include adipate, azelate, enzoate, citrate, stearate, isoebucate, sebacate, triethyl citrate, tri-n-butyl citrate, acetyl tri-n-butyl citrate, citric acid esters, and those described in the Encyclopedia of Polymer Science and Technology, Vol. 10 (1969), published by John Wiley & Sons. The preferred plasticizers are triacetin, acetylated monoglyceride, grape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, and the like. Depending on the particular plasticizer, amounts of from 0 to about 25%, and preferably about 2% to about 15% of the plasticizer can be used based upon the total weight of the coating.

As used herein the term passageway includes an aperture, orifice, bore, hole, weaken area or an erodible element such as a gelatin plug that erodes to form an osmotic passageway for the release of the antihyperglycemic drug from the dosage form. A detailed description of the passageway can be found in U.S. Pat. Nos. 3,845,770, 3,916,899, 4,034,758, 4,077,407, 4,783,337 and 5,071,607.

Generally, the membrane coating around the core will comprise from about 1% to about 5% and preferably about 2% to about 3% based on the total weight of the core and coating.

In an alternative embodiment, the dosage form of the present invention may also comprise an effective amount of the antihyperglycemic drug that is available for immediate release. The effective amount of antihyperglycemic drug for immediate release may be coated onto the semipermeable membrane of the dosage form or it may be incorporated into the semipermeable membrane.

In a preferred embodiment the dosage form will have the following composition:

|  | Preferred | Most Preferred |
|---|---|---|
| CORE: |  |  |
| drug | 50-98% | 75-95% |
| binder | 0-40% | 3-15% |
| absorption enhancer | 0-20% | 2-10% |
| COATING: |  |  |
| semipermeable polymer | 50-99% | 75-95% |
| flux enhancer | 0-40% | 2-20% |
| plasticizer | 0-25% | 2-15% |

The dosage forms prepared according to the present invention should exhibit the following dissolution profile when tested in a USP type 2 apparatus at 75 rpms in 900 ml of simulated intestinal fluid (pH 7.5 phosphate buffer) and at 37° C.:

| Time (hours) | Preferred | Most Preferred |
|---|---|---|
| 2 | 0-25% | 0-15% |
| 4 | 10-45% | 20-40% |
| 8 | 30-90% | 45-90% |
| 12 | NTL 50% | NTL 60% |
| 16 | NTL 60% | NTL 70% |
| 20 | NTL 70% | NTL 80% |

NTL = NOT LESS THAN

In the preparation of the tablets of the invention, various conventional well known solvents may be used to prepare the granules and apply the external coating to the tablets of the invention. In addition, various diluents, excipients, lubricants, dyes, pigments, dispersants etc. which are disclosed in Remington's Pharmaceutical Sciences, 1995 Edition may be used to optimize the formulations of the invention.

DESCRIPTION OF THE PREFERRED EMBODIMENTS

Example 1

A controlled release tablet containing 850 mg of metformin HCl and having the following formula is prepared as follows:

| I Core |  |
|---|---|
| metformin HCl | 90.54% |
| povidone[1], USP | 4.38% |
| sodium tribasic phosphate | 4.58% |
| magnesium stearate | 0.5% |

[1]approximate molecular weight = 50,000; dynamic viscosity (10% w/v solution at 20° C.) = 5.5-8.5 m Pa s.

(a) Granulation

The metformin HCl is delumped by passing it through a 40 mesh screen and collecting it in a clean, polyethylene-lined container. The povidone, K-30, and sodium tribasic phosphate are dissolved in purified water. The delumped metformin HCl is then added to a top-spray fluidized bed granulator and granulated by spraying the binding solution of povidone and sodium tribasic phosphate under the following conditions: inlet air temperature of 50-70° C.; atomization air pressure of 1-3 bars; and spray rate of 10-100 ml/min.

Once the binding solution is depleted, the granules are dried in the granulator until the loss on drying is less than 2%. The dried granules are passed through a Comil equipped with the equivalent of an 18 mesh screen.

(b) Tableting

The magnesium stearate is passed through a 40 mesh stainless steel screen and blended with the metformin HCl granules for approximately five (5) minutes. After blending, the granules are compressed on a rotary press fitted with 15/32" round standard concave punches (plain lower punch, upper punch with an approximately 1 mm indentation pin).

(c) Seal Coating (optional)

The core tablet is seal coated with an Opadry material or other suitable water-soluble material by first dissolving the Opadry material, preferably Opadry Clear, in purified water. The Opadry solution is then sprayed onto the core tablet using a pan coater under the following conditions: exhaust air temperature of 38-42° C.; atomization pressure of 28-40 psi; and spay rate of 10-15 ml/min. The core tablet is coated with the sealing solution until a theoretical coating level of approximately 2% is obtained.

| II Sustained Release Coating |  |
|---|---|
| cellulose acetate (398-10)[2] | 85% |
| triacetin | 5% |
| PEG 400 | 10% |

[2]acetyl content 39.3-40.3%

(d) Sustained Release Coating

The cellulose acetate is dissolved in acetone while stirring with a homogenizer. The polyethylene glycol 400 and triacetin are added to the cellulose acetate solution and stirred until a clear solution is obtained. The clear coating solution is then sprayed onto the seal coated tablets in a fluidized bed coater employing the following conditions: product temperature of 16-22° C.; atomization pressure of approximately 3 bars; and spray rate of 120-150 ml/min. The sealed core tablet is coated until a theoretical coating level of approximately 3% is obtained.

The resulting tablet is tested in simulated intestinal fluid (pH 7.5) and simulated gastric fluid (SGF) according to the procedure described in United States Pharmacopeia XXIII, Apparatus 2 @ 75 rpm and found to have the following release profile:

| TIME (hours) | % Released (SGF) | % Released (pH 7.5) |
|---|---|---|
| 2 | 9 | 12 |
| 4 | 27 | 32 |
| 8 | 62 | 82 |
| 12 | 82 | 100 |
| 16 | 88 | 105 |
| 20 | 92 | 108 |

The release profile in pH 7.5 and SGF of the sustained release product prepared in this Example is shown in FIG. 1.

Figure 4:
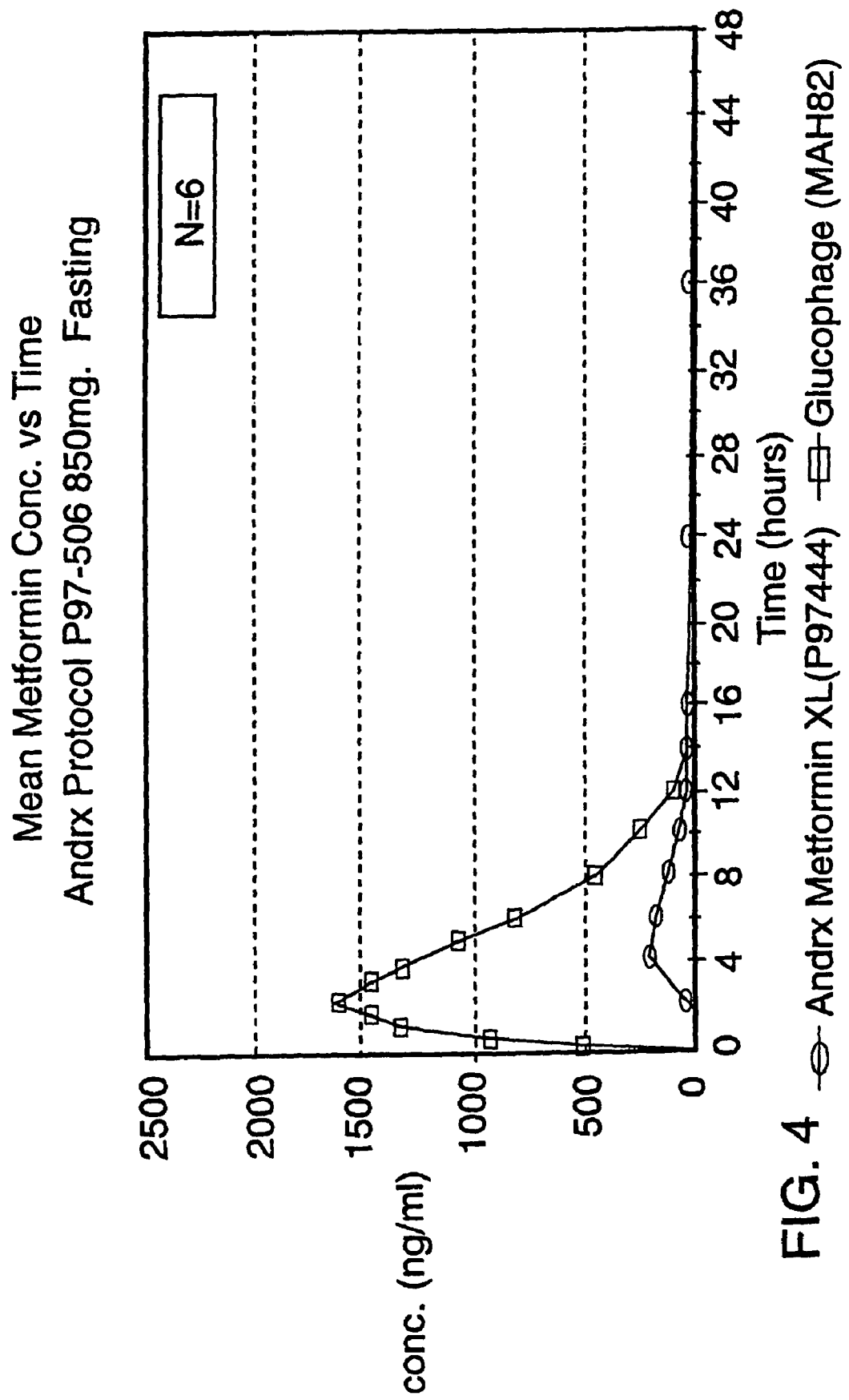
FIG. 4 is a graph depicting the in vivo metformin plasma profile of the formulation described in Example 1 and the in vivo metformin plasma profile of the commercially available metformin HCl product GLUCOPHAGE® under fasting conditions.

FIG. 4 depicts the in vivo metformin plasma profile of the sustained release product prepared in this Example. Also shown in FIG. 4 is the in vivo metformin plasma profile of GLUCOPHAGE®, a commercially available pharmaceutical product containing the drug metformin HCl.

Example 2

A controlled release tablet containing 850 mg of metformin HCl and having the following formula is prepared as follows:

| I Core | |
|---|---|
| metformin HCl | 88.555% |
| povidone[3], USP | 6.368% |
| sodium lauryl sulfate | 4.577% |
| magnesium stearate | 0.5% |

[3]approximate molecular weight = 1,000,000, dynamic viscosity (10% w/v solution at 20° C.) = 300-700 m Pa s.

(a) Granulation.

The metformin HCl and sodium lauryl sulfate are delumped by passing them through a 40 mesh screen and collecting them in a clean, polyethylene-lined container. The povidone, K-90F, is dissolved in purified water. The delumped metformin HCl and sodium lauryl sulfate are then added to a top-spray fluidized bed granulator and granulated by spraying with the binding solution of povidone under the following conditions: inlet air temperature of 50-70° C.; atomization air pressure of 1-3 bars; and spray rate of 10-100 ml/min.

Once the binding solution is depleted, the granules are dried in the granulator until the loss on drying is less than 2%. The dried granules are passed through a Comil equipped with the equivalent of an 18 mesh screen.

(b) Tableting

The magnesium stearate is passed through a 40 mesh stainless steel screen and blended with the metformin HCl granules for approximately five (5) minutes. After blending, the coated granules are compressed on a rotary press fitted with 15/32" round standard concave punches (plain lower punch, upper punch with an approximately 1 mm indentation pin).

(c) Seal Coating (optional)

The core tablet is seal coated with an Opadry material or other suitable water-soluble material by first dissolving the Opadry material, preferably Opadry Clear in purified water. The Opadry solution is then sprayed onto the core tablet using a pan coater under the following conditions: exhaust air temperature of 38-42° C.; atomization pressure of 28-40 psi; and spay rate of 10-15 ml/min. The core tablet is coated with the sealing solution until a theoretical coating level of approximately 2% is obtained.

| II Sustained Release Coating | |
|---|---|
| cellulose acetate (398-10)[4] | 85% |
| triacetin | 5% |
| PEG 400 | 10% |

[4]acetyl content 39.3-40.3%

(d) Sustained Release Coating

The cellulose acetate is dissolved in acetone while stirring with a homogenizer. The polyethylene glycol 400 and triacetin are added to the cellulose acetate solution and stirred until a clear solution is obtained. The clear coating solution is then sprayed onto the seal coated tablets in a fluidized bed coater employing the following conditions: product temperature of 16-22° C.; atomization pressure of approximately 3 bars; and spray rate of 120-150 ml/min. The sealed core tablet is coated until a theoretical coating level of approximately 3% is obtained.

The resulting tablet is tested in simulated intestinal fluid (pH 7.5) and simulated gastric fluid (SGF) according to the procedure described in United States Pharmacopeia XXIII, Apparatus 2 @ 75 rpm and found to have the following release profile:

| TIME (hours) | % Released (SGF) | % Released (pH 7.5) |
|---|---|---|
| 2 | 13 | 12 |
| 4 | 29 | 27 |
| 8 | 55 | 52 |
| 12 | 72 | 71 |
| 16 | 81 | 83 |
| 20 | 87 | 91 |

Figure 2:
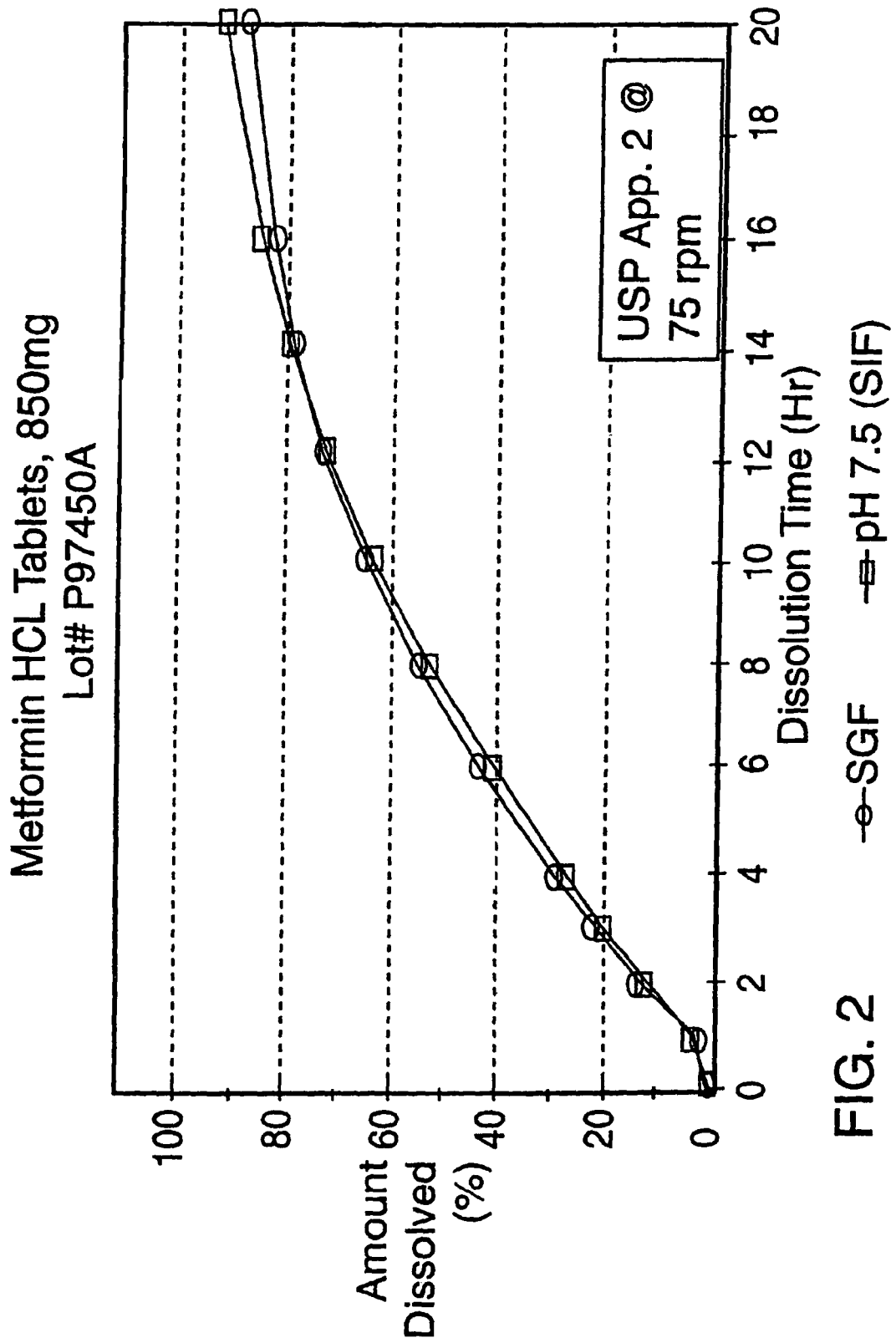
FIG. 2 is a graph which depicts the dissolution profile in simulated intestinal fluid (pH 7.5 phosphate buffer) and simulated gastric fluid (SGF) of the formulation described in Example 2 as tested according to the procedure described in United States Pharmacopeia XXIII, Apparatus 2 @ 75 rpm.

The release profile in pH 7.5 and SGF of the sustained release product prepared in this Example is shown in FIG. 2.

Figure 5:
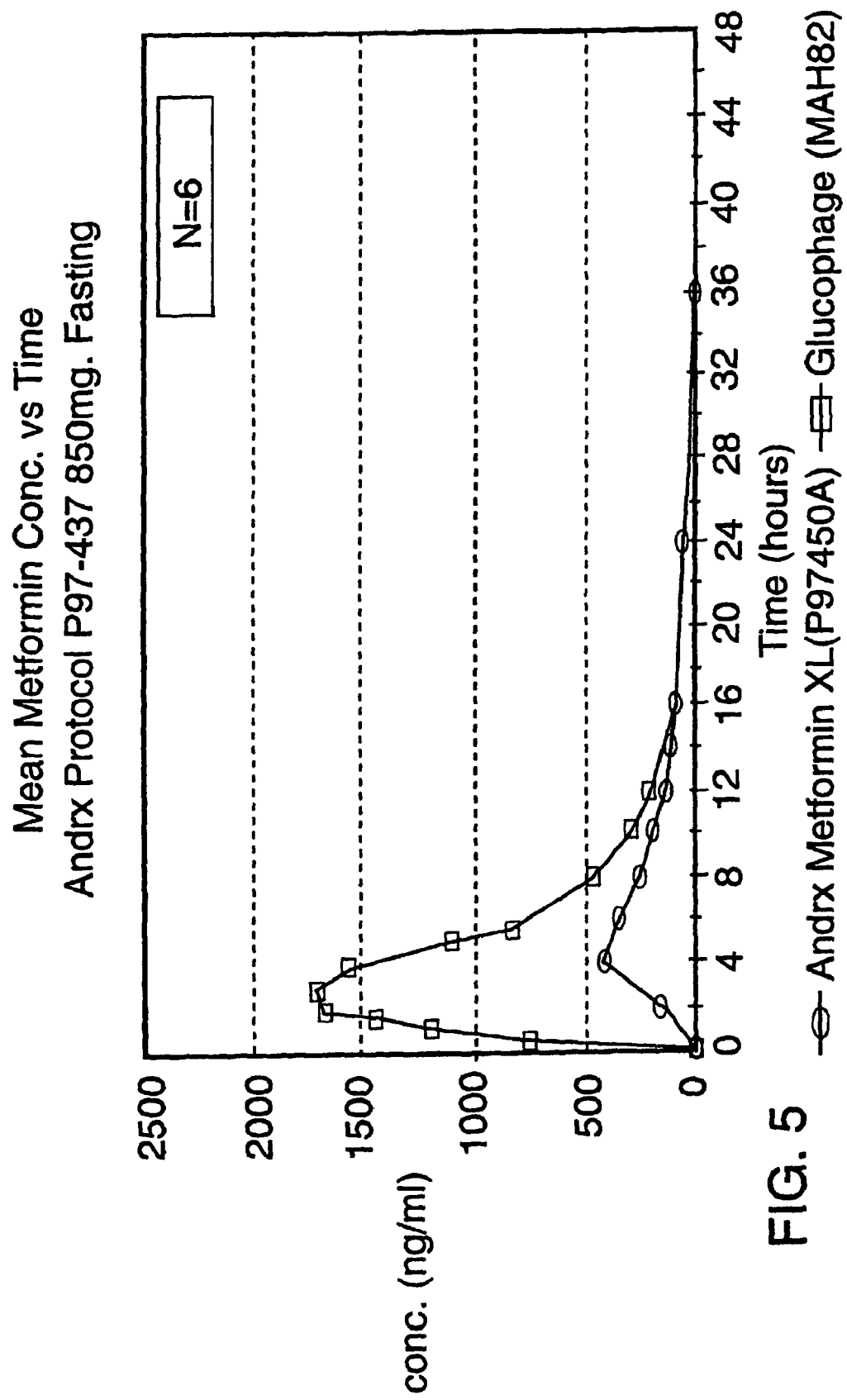
FIG. 5 is a graph depicting the in vivo metformin plasma profile of the formulation described in Example 2 and the in vivo metformin plasma profile of the commercially available metformin HCl product GLUCOPHAGE® under fasting conditions.

FIG. 5 depicts the in vivo metformin plasma profile of the sustained release product prepared in this Example under fasting conditions. FIG. 5 also shows the in vivo metformin plasma profile of the GLUCOPHAGE® product under fasting conditions.

Figure 6:
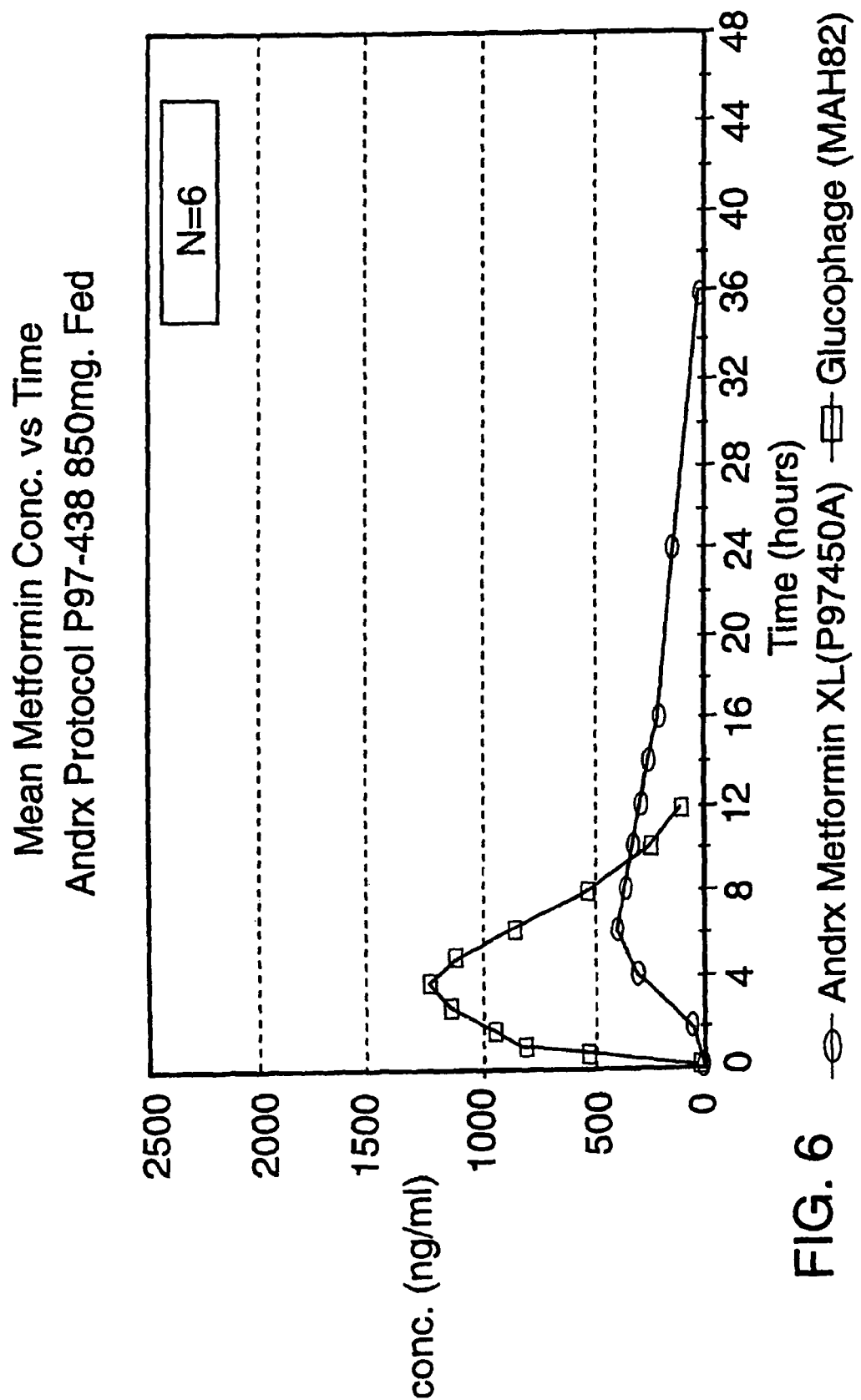
FIG. 6 is a graph depicting the in vivo metformin plasma profile of the formulation described in Example 2 and the in vivo metformin plasma profile of the commercially available metformin HCl product GLUCOPHAGE® under fed conditions.

FIG. 6 depicts the in vivo metformin plasma profile of the sustained release product prepared in this Example under fed conditions. FIG. 6 also shows the in vivo metformin plasma profile of the GLUCOPHAGE® product under fed conditions.

FIGS. 5 and 6 clearly show that the dosage forms prepared in accordance with the present invention exhibit consistent bioavailability under both fed and fasting conditions while the GLUCOPHAGE® product's bioavailability decreases in the presence of food.

Example 3

A controlled release tablet containing 850 mg of metformin HCl and having the same formula as in Example 2 is prepared as described in Example 2 except that an additional hole was drilled on the plain side of the coated tablet. The additional hole had a diameter of approximately 1 mm.

The resulting tablet is tested in simulated intestinal fluid (pH 7.5) and simulated gastric fluid (SGF) according to the procedure described in United States Pharmacopeia XXIII, Apparatus 2 @ 75 rpm and found to have the following release profile:

| TIME (hours) | % Released (SGF) | % Released (pH 7.5) |
|---|---|---|
| 2 | 13 | 14 |
| 4 | 27 | 28 |
| 8 | 50 | 63 |
| 12 | 67 | 84 |
| 16 | 84 | 95 |
| 20 | 97 | 102 |

Figure 3:
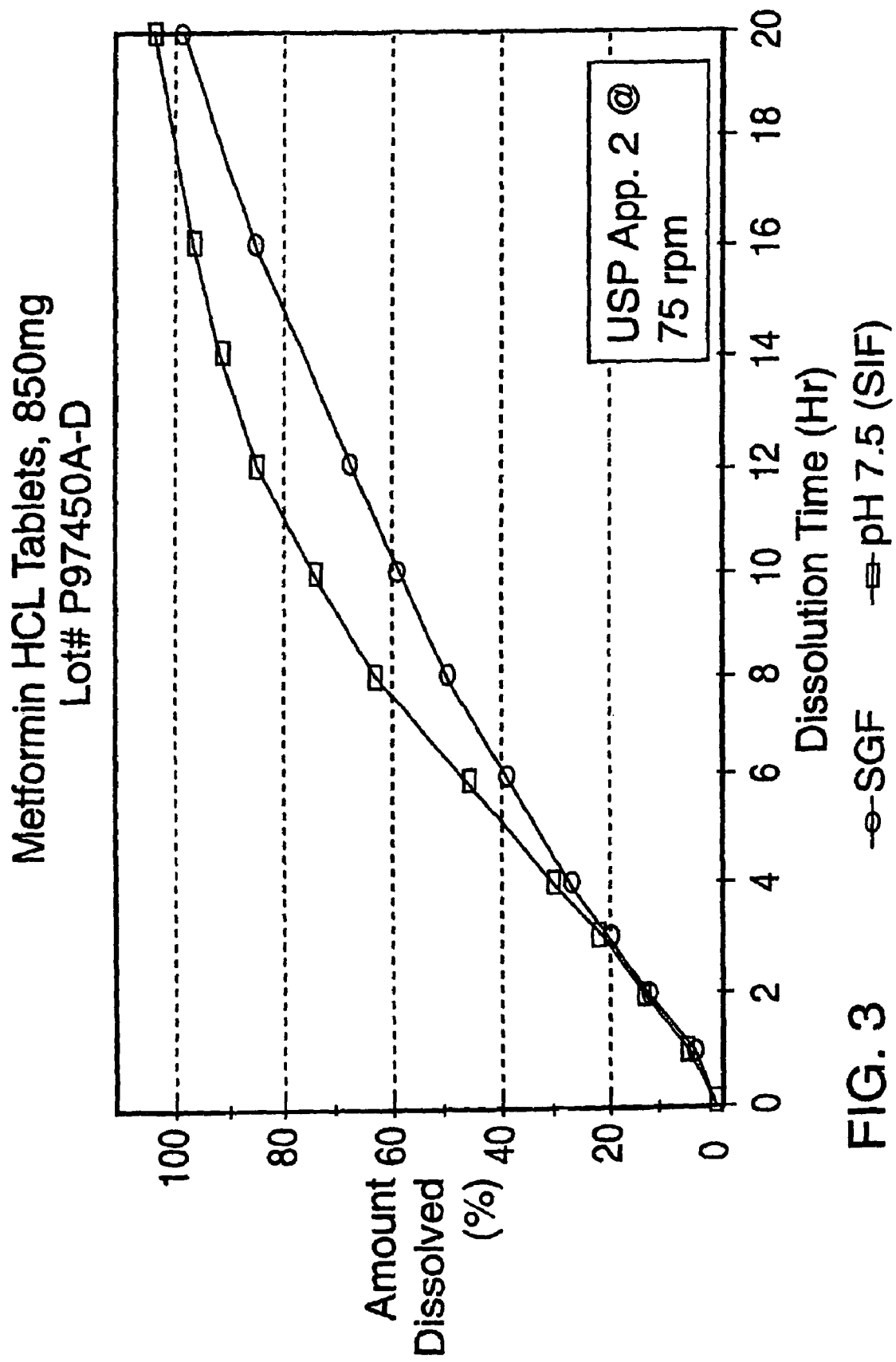
FIG. 3 is a graph which depicts the dissolution profile in simulated intestinal fluid (pH 7.5 phosphate buffer) and simulated gastric fluid (SGF) of the formulation described in Example 3 as tested according to the procedure described in United States Pharmacopeia XXIII, Apparatus 2 @ 75 rpm.

The release profile in pH 7.5 and SGF of the sustained release product prepared in this Example is shown in FIG. 3.

Figure 7:
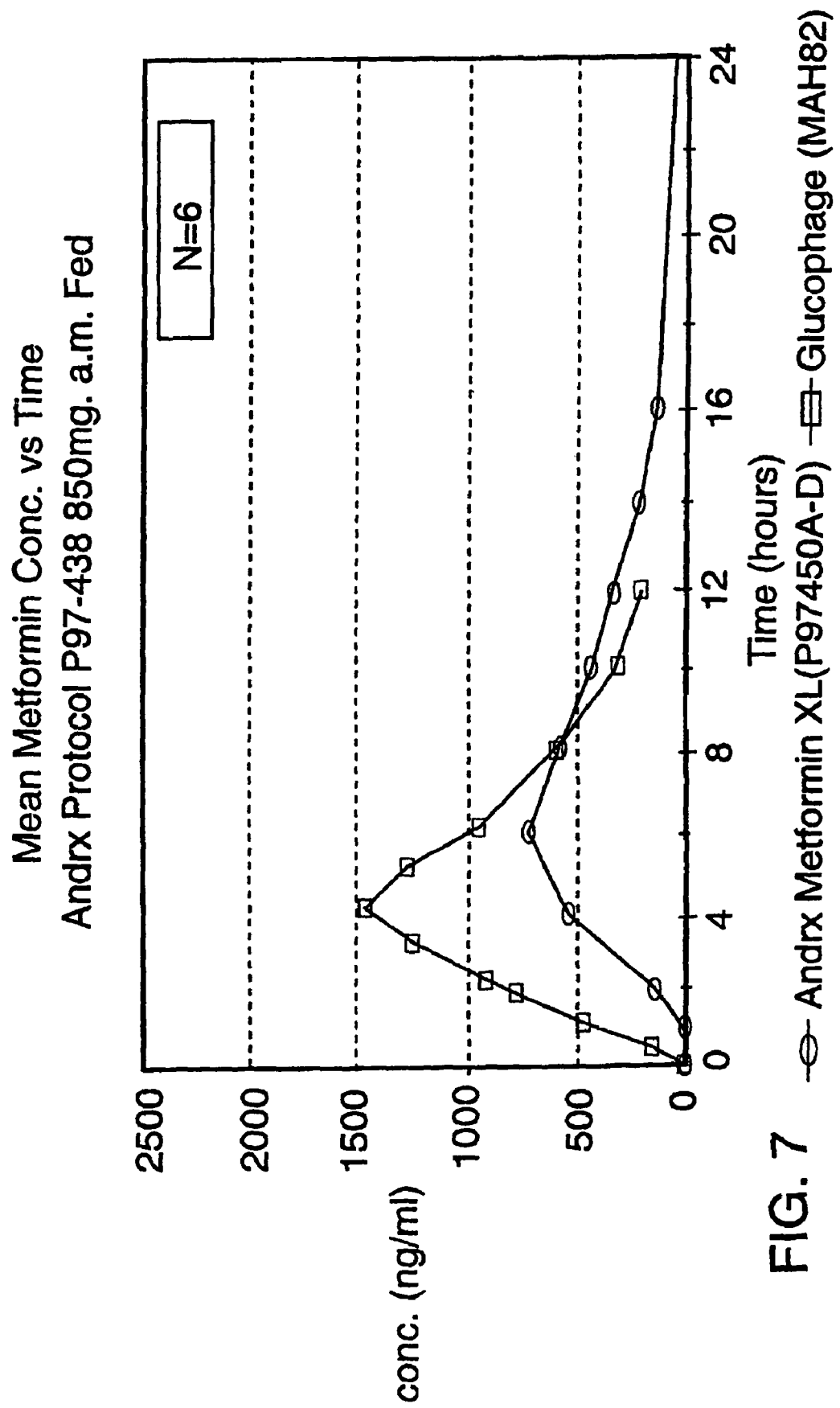
FIG. 7 is a graph depicting the in vivo metformin plasma profile of the formulation described in Example 3 and the in vivo metformin plasma profile of the commercially available metformin HCl product GLUCOPHAGE® under fed conditions (after breakfast).

FIG. 7 depicts the in vivo metformin plasma profile of the sustained release product prepared in this Example when administered shortly after breakfast. FIG. 7 also shows the in vivo metformin plasma profile of the GLUCOPHAGE® product administered shortly after breakfast.

Figure 8:
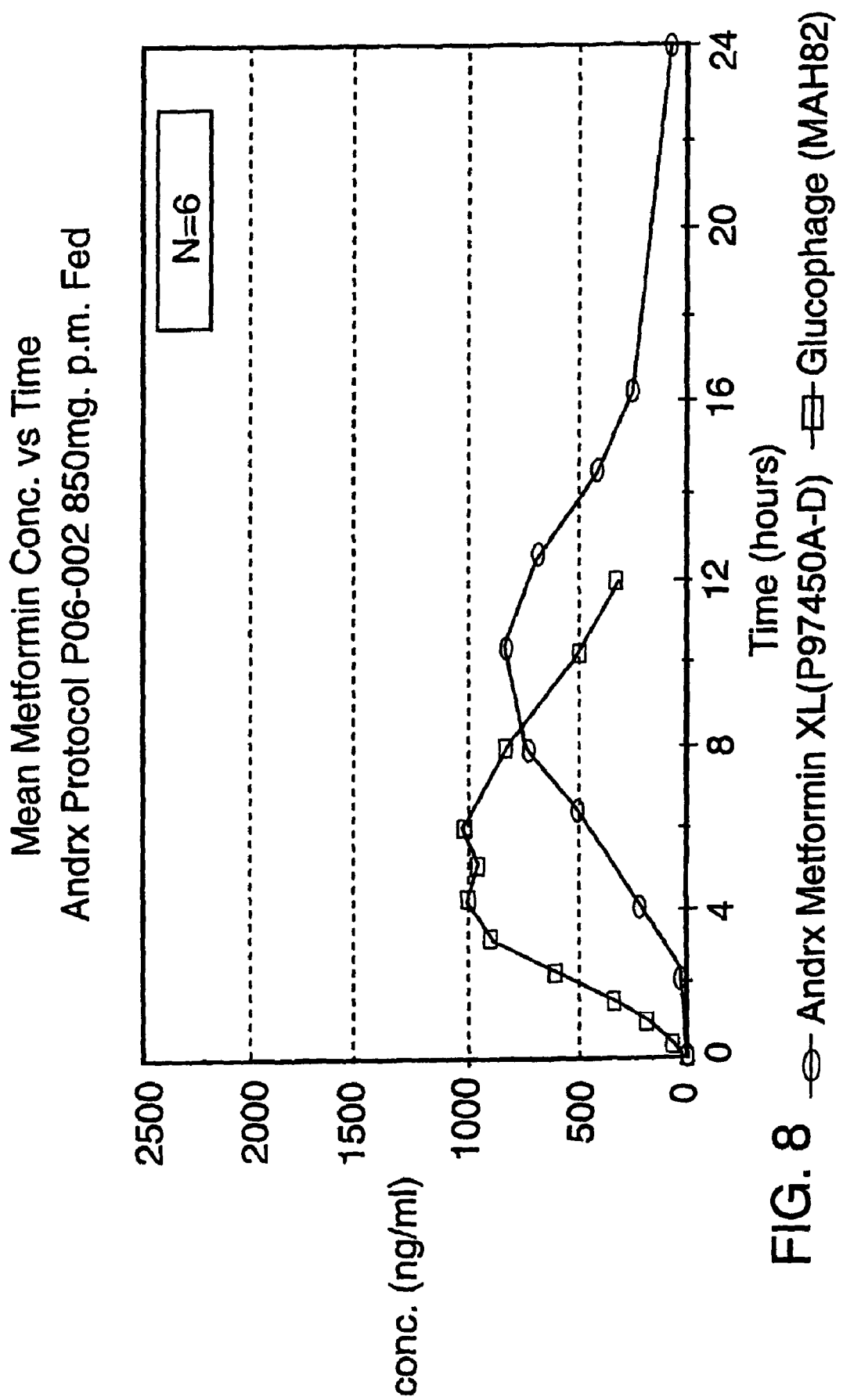
FIG. 8 is a graph depicting the in vivo metformin plasma profile of the formulation described in Example 3 and the in vivo metformin plasma profile of the commercially available metformin HCl product GLUCOPHAGE® under fed conditions (after dinner).

FIG. 8 depicts the in vivo metformin plasma profile of the sustained release product prepared in this Example when administered shortly after dinner. FIG. 8 also shows the in vivo metformin plasma profile of the GLUCOPHAGE® product administered shortly after dinner.

Table 1 is a summary of the bioavailability comparision data, test/reference ratio, shown in FIGS. 4-8 wherein the GLUCOPHAGE® product is the reference product in a two way crossover biostudy with n=6.

TABLE 1

| Formula | Figure | Study | AUC | Cmax | Tmax |
|---|---|---|---|---|---|
| Ex. 1 | 4 | Fasting | 0.202 | 0.12 | 2.15 |
| Ex. 2 | 5 | Fasting | 0.369 | 0.214 | 1.73 |
| Ex. 2 | 6 | Fed (bkft) | 0.628 | 0.305 | 1.94 |
| Ex. 3 | 7 | Fed (bkft) | 0.797 | 0.528 | 1.82 |
| Ex. 3 | 8 | Fed (dinner) | 0.850 | 0.751 | 2.00 | bkft = breakfast

The results reported in Table 1 and FIGS. 4-8 show that dosage forms prepared in accordance with the present invention exhibit an increase in the bioavailability of the antihyperglycemic drug in the presence of food, especially when taken with or shortly after the evening meal.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:

1. A method of treating a human diabetic patient with an oral solid sustained release tablet of metformin hydrochloride, comprising: administering the sustained release tablet to the human diabetic patient once a day under fed conditions, wherein the sustained release tablet comprises (i) metformin hydrochloride and (ii) a sustained release material, wherein the tablet does not employ an expanding polymer, the sustained release tablet provides therapeutic plasma levels of said metformin to the human patient over a 12 to 24 hour period after administration; and the sustained release tablet exhibits the following in vitro dissolution profile when tested in a USP Type 2 apparatus at 75 rpms in 900 ml of a pH 7.5 phosphate buffer and 37° C.:

0-25% of the metformin is released after 2 hours;
10-45% of the metformin is released after 4 hours;
30-90% of the metformin is released after 8 hours;
not less than 50% of the metformin is released after 12 hours;
not less than 60% of the metformin is released after 16 hours and not less than 70% of the metformin is released after 20 hours.

2. The method as defined in claim 1 wherein the tablet exhibits the following in vitro dissolution profile when tested in a USP Type 2 apparatus at 75 rpms in 900 ml of a pH 7.5 phosphate buffer and 37° C.:

0-15% of the metformin is released after 2 hours;
20-40% of the metformin is released after 4 hours;
45-90% of the metformin is released after 8 hours;
not less than 60% of the metformin is released after 12 hours;
not less than 70% of the metformin is released after 16 hours and
not less than 80% of the metformin is released after 20 hours.

3. The method of claim 1 wherein the tablet is administered with or after a meal.

4. The method of claim 1 wherein the tablet is administered with or after evening meal.

5. The method of claim 1 wherein the tablet is an osmotic tablet with a homogeneous osmotic core.

* * * * *